(12) United States Patent
Dennis

(10) Patent No.: US 8,211,480 B1
(45) Date of Patent: Jul. 3, 2012

(54) METHOD FOR ENVIRONMENTAL REMEDIATING TO REDUCE INCIDENCE OF SINUSITIS

(76) Inventor: Donald Patrick Dennis, Atlanta, GA (US)

( * ) Notice: Subject to any disclaimer, the term of this patent is extended or adjusted under 35 U.S.C. 154(b) by 0 days.

(21) Appl. No.: 13/342,939

(22) Filed: Jan. 3, 2012

Related U.S. Application Data

(62) Division of application No. 12/573,791, filed on Oct. 5, 2009, now Pat. No. 8,088,481.

(51) Int. Cl.
*A01N 65/00* (2009.01)

(52) U.S. Cl. ...................................................... 424/725

(58) Field of Classification Search .................. None
See application file for complete search history.

(56) References Cited

U.S. PATENT DOCUMENTS

2004/0071797 A1* 4/2004 Dennis et al. ................. 424/736

* cited by examiner

*Primary Examiner* — Michael Meller
(74) *Attorney, Agent, or Firm* — Sanford J. Asman

(57) ABSTRACT

The invention provides a method for remediating environmental fungal sites in an environment to which a patient experiencing sinusitis and chronic rhino sinusitis brought on by fungal antigens is exposed. The formulation includes grapefruit seed extract, together with lemon, lime, and tangerine seed extracts. The method removes both air borne antigens and mold colonies from the environment.

2 Claims, No Drawings

METHOD FOR ENVIRONMENTAL REMEDIATING TO REDUCE INCIDENCE OF SINUSITIS

CROSS-REFERENCE TO RELATED APPLICATIONS

The present invention is a division U.S. patent application Ser. No. 12/573,791, which issued as U.S. Pat. No. 8,088,418 on Jan. 3, 2012, which is a continuation-in-part of U.S. patent application Ser. No. 11/420,887, filed May 30, 2006, which is a continuation of U.S. patent application Ser. No. 60/685,721, filed May 27, 2005, each filed by the present inventor, the contents and priority of each of which are claimed herein.

The present application also claims the priority of U.S. provisional application Ser. No. 61/102,361 filed Oct. 3, 2009.

BACKGROUND OF THE INVENTION

The present invention relates to a method for remediating environmental conditions in order to reduce the incidence of sinusitis of persons exposed to such conditions.

In treating patients with sinusitis, it has been found that in a significant portion of such patients the sinusitis was brought on by fungal antigens which are infecting the patient and within the patient's sinus and nasal passages. In examining the environmental conditions to which such patients are exposed, it has been found that such conditions include areas in which there is a significant mold count. Accordingly, while one aspect of the successful treatment of such patients has involved removing any fungal antigens from the patient through a series of steps which are the subject of a copending patent application by the present inventor, a significant aspect of their treatment also involves the remediation of the environmental conditions to which they were, and continue to be, exposed.

SUMMARY OF THE INVENTION

In accordance with the present invention, a method for remediating environmental conditions to remove fungal antigens has been developed. The method involves treating sinusitis caused by fungus comprising the steps of removing fungal antigens from the sinus of the patient and removing fungus from the environment to which the patient is exposed.

DETAILED DESCRIPTION OF THE PREFERRED EMBODIMENT

The method for remediating environmental conditions to which patients experiencing sinusitis caused by fungus comprises the steps of filtering the air to remove air borne antigens and treating the environment with antifungal agents to destroy any fungus present.

In accordance with the foregoing, air borne fungal antigens are first removed by HEPA air filters placed in each room in which the patient occupies. The purpose of the HEPA air filtration is to remove, from the air, breathed by the patient, as many of the air borne antigens as possible in order to prevent further infection to the patient undergoing treatment (or who has undergone such treatment). In accordance with the present invention, true HEPA air filters, such as the one manufactured by IQ Air (See, http://www.iqair.us/iq-air.html) should be placed in and used in each room occupied by the patient.

The next step in the remediation process is to reduce the mold count in any rooms occupied by the patient. It has been found that the use of an antifungal agent, such as a CitriDrop® evaporation container (with wick), left in each room the patient occupies is capable of reducing mold counts to zero in a 12 foot by 12 foot space within three days. Accordingly, an appropriate number (based on the number and size of the rooms occupied by the patient) should also be placed in each area occupied by the patient.

Next, the areas occupied by the patient should be sprayed with CitriSpray® environmental spray to further insure that the areas have had their mold sources destroyed. Thereafter, a CitriDrop® candle should be burned in each room in which the patient spends an hour or more in daily, with the candle being burned for three hours on the first day and for one hour each day thereafter. The burning of the CitriDrop® candles further insures that any difficult to reach mold population will be exposed to the antifungal agents in the candles.

Both the CitriSpray® and CitriDrop® products are formulated with grapefruit seed extract, together with lemon, lime, and tangerine seed extracts which have been found to be able to reduce mold count and destroy environmental mold colonies.

I claim:

1. A method of treating fungal sinusitis in a patient in need thereof comprising the steps of:
    (a) filtering the air in each room which the patient occupies to remove air borne fungal antigens; and
    (b) evaporating a solution containing therapeutically effective amounts of grapefruit seed extract, lemon seed extract, lime seed extract, and tangerine seed extract in each room in which the patient spends an hour or more daily, using a sufficient amount of said solution for a time sufficient to destroy all mold sources in each said room, and wherein said sinusitis in the patient is treated by evaporating the solution.

2. The method of claim 1 wherein said step of filtering is accomplished using a HEPA air filter.

* * * * *